United States Patent [19]
Leveskis

[11] 3,945,940
[45] Mar. 23, 1976

[54] PREPARATION OF ALDEHYDE AND KETONE ORGANIC PEROXIDE COMPOSITIONS

[75] Inventor: Newton G. Leveskis, Walnut Creek, Calif.

[73] Assignee: Argus Chemical Corporation, Brooklyn, N.Y.

[22] Filed: June 4, 1970

[21] Appl. No.: 43,329

Related U.S. Application Data

[63] Continuation-in-part of Ser. No. 702,782, Feb. 5, 1968, which is a continuation-in-part of Ser. No. 473,855, July 21, 1965, abandoned.

[52] U.S. Cl............. 252/186; 260/610 R; 252/426; 260/861
[51] Int. Cl.$^2$.................. C07C 179/06; A61L 13/04
[58] Field of Search............ 260/610 R, 610 A, 338, 260/586 R, 590, 593 A, 593 R, 861; 252/426, 186

[56] References Cited
UNITED STATES PATENTS

| 2,092,322 | 9/1937 | Moser | 260/610 R |
|---|---|---|---|
| 2,133,733 | 10/1938 | Moser | 260/610 R |
| 2,270,175 | 1/1942 | Tadema | 260/610 R |
| 2,424,851 | 7/1947 | Rudoff | 260/338 |
| 3,047,406 | 7/1962 | Ferrari | 99/232 |
| 3,149,126 | 9/1964 | Milas | 260/338 |
| 3,546,249 | 12/1970 | Gerritsen | 260/338 |

OTHER PUBLICATIONS

Tobolsky, "Organic Peroxide," pp. 1, 2 and 44–51, (1954).

Hawkins, "Organic Peroxide," pp. 22, 23 and 139–141, (1961).

*Primary Examiner*—Bernard Helfin
*Assistant Examiner*—W. B. Lone
*Attorney, Agent, or Firm*—Townsend and Townsend

[57] ABSTRACT

Improved organic aldehyde and ketone peroxide compositions useful for initiating the polymerization of polyesters formed from the concurrent reaction of a beta dione such as 2,4-pentanedione and a different (non-beta dione) ketone or aldehyde, for example methyl ethyl ketone, with aqueous hydrogen peroxide.

26 Claims, 4 Drawing Figures

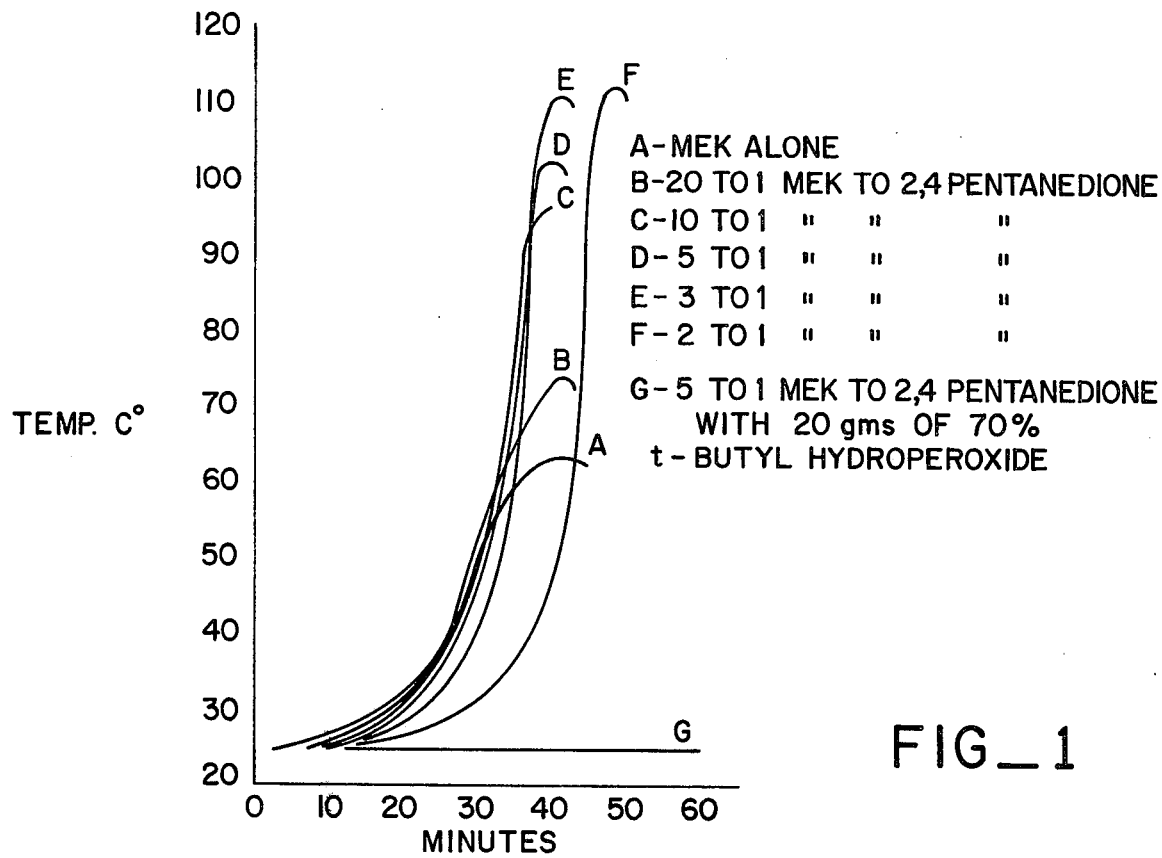
FIG_1
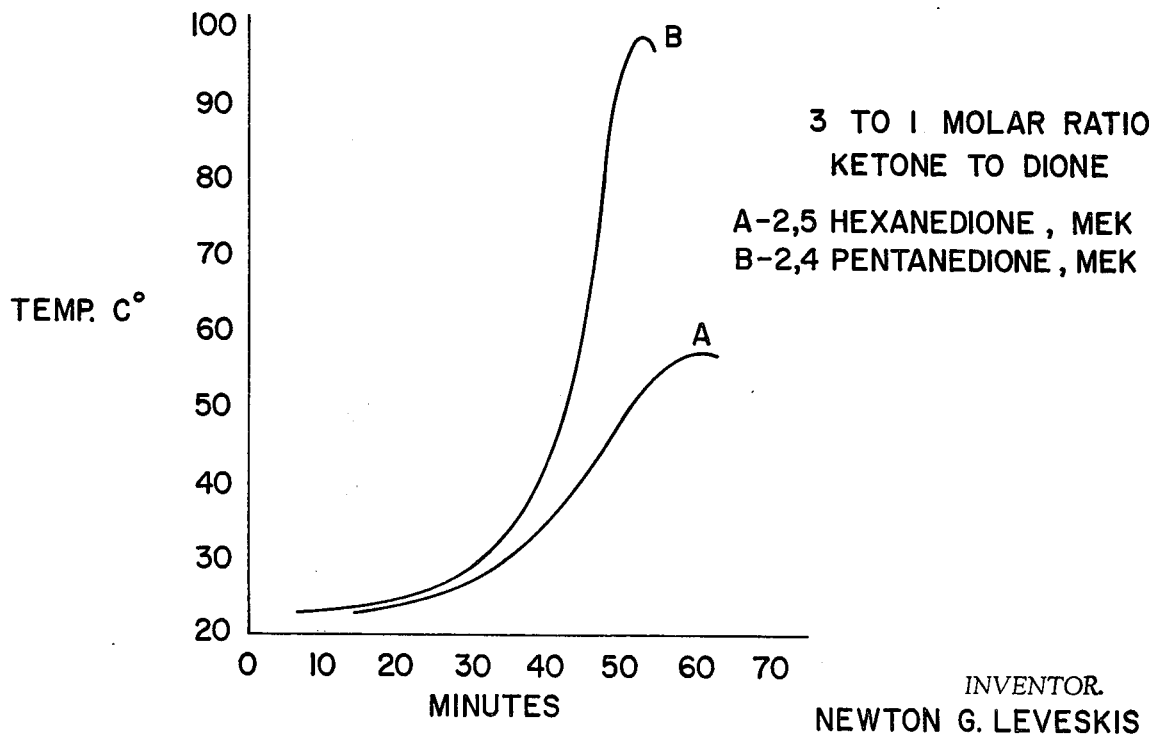
FIG_2

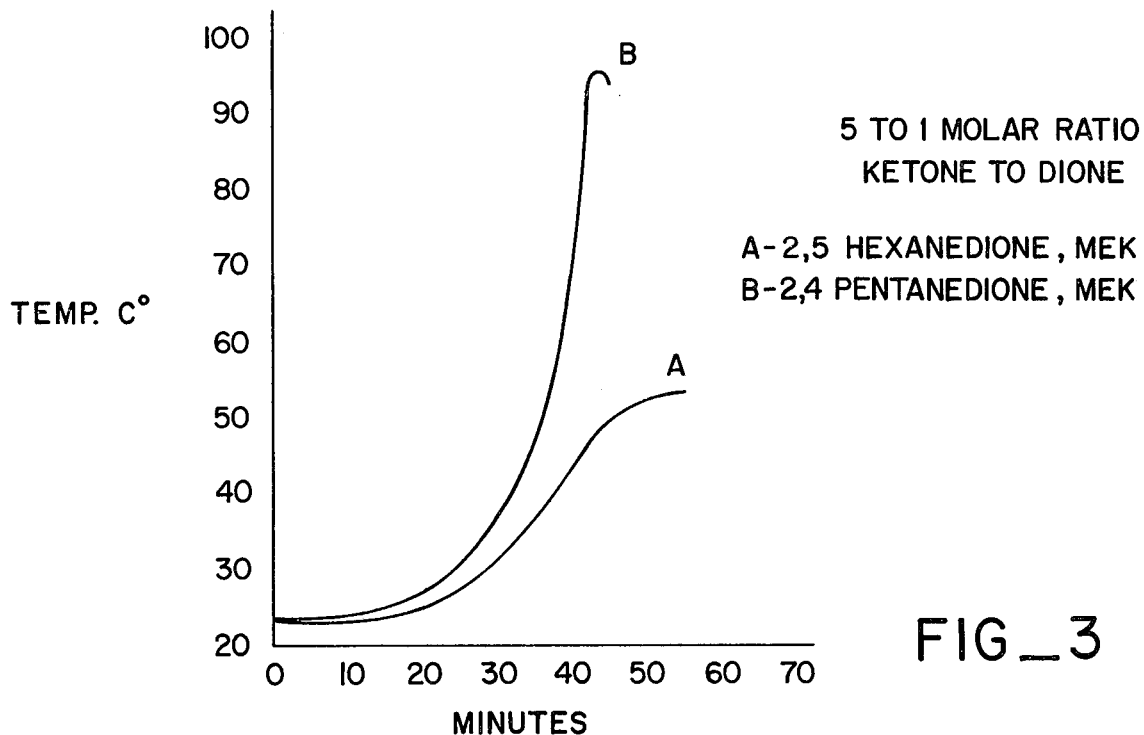
FIG_3
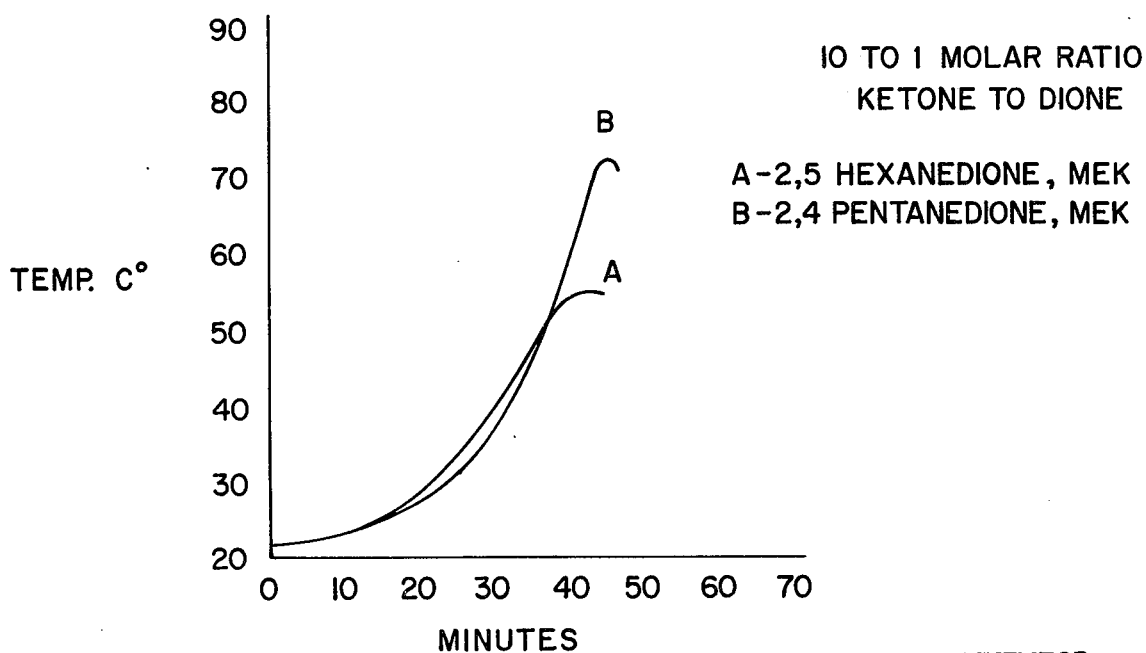
FIG_4

PREPARATION OF ALDEHYDE AND KETONE ORGANIC PEROXIDE COMPOSITIONS

This is a continuation-in-part of copending patent application Ser. No. 702,782, filed Feb. 5, 1968, which in turn is a continuation-in-part of Ser. No. 473,855, filed July 21, 1965, now abandoned.

This invention relates to improved organic ketone and aldehyde peroxide compositions, to a method for their preparation, and to their use as polymerization initiators. In a preferred embodiment, a fire resistant organic ketone peroxide is provided that has advantages in catalyzing polyester resins.

The present invention departs from and improves upon earlier teachings through the use of a novel combination of peroxides formed concurrently from an aldehyde or ketone (other than a beta dione) such as methyl ethyl ketone and a beta dione such as 2,4-pentanedione. The beta dione and nonbeta dione ketone or aldehyde are co-reacted with hydrogen peroxide in conventional fashion to form a mixture of organic peroxides. The chemical structure of the end products found in the mixture is not known with certainty but is believed to be a variety of peroxide isomers and polymers in which both the methyl ethyl ketone or other ketone or aldehyde and 2,4-pentanedione or other dione collectively participate. The terms "co-reaction product" and "mixture" are used herein to describe these new peroxides synthesized from the combination of the selected aldehyde or ketone and beta dione with hydrogen peroxide.

In the preferred embodiment, the new peroxide co-reaction product is made in combination with water and a mutual solvent or dispersant in accordance with copending patent application Ser. No. 584,608, filed Oct. 5, 1966, now U.S. Pat. No. 3,507,800, and is surprisingly stable and fire resistant. As a result, compositions containing about 35–60% of the organic peroxides by weight can be prepared and the desired fire resistance still obtained. Thus, a composition has been prepared in large quantities containing 52% of the co-reaction of 2,4-pentanedione and methyl ethyl ketone that is so flame resistant that it has been approved by the Bureau of Explosives as being not subject to classification as an oxidizing material under Interstate Commerce Commission regulations.

Perhaps the most significant advantages of the new compositions (whether made with sufficient water to be fire resistant or not) relate to their utility as catalysts for polyester resins. Over a broad spectrum of the various polyester resins utilized commercially the new materials have proved superior on the average in the important characteristics desired in an organic peroxide catalyst. The new compositions when used with polyester resins exhibit faster gel times, higher peak temperatures, and shorter times to reach the peak temperature than has been possible with previously available catalyst systems of the same type. The present invention therefore provides compositions of broad utility that will satisfy the needs of the vast majority of catalyst users and will avoid the necessity of choosing a special catalyst depending upon the particular resin system being utilized. The present materials will give excellent results in almost all cases at room temperature and in most instances will be superior to all competitive peroxide catalysts. Without intention of limiting the invention as claimed it is believed that the beta dione contributes the high peak temperatures while the other ketone or aldehyde contributes the fast gel times observed when using the new peroxide compositions.

The essential reactants for making the new compositions are hydrogen peroxide, a beta dione, and a different, i.e. a non-beta dione or an aldehyde. Any different ketone or aldehyde is contemplated if it will coreact with the selected beta dione in the presence of hydrogen peroxide to form an organic peroxide co-reaction product so long as it is not a beta dione. Preferably, the selected aldehyde or different ketone, or mixture thereof, is free from aliphatic unsaturation. Otherwise, virtually any organic compound containing one or more aldehyde or ketone carbonyl groups may be selected with excellent results. Thus, both alkyl and aromatic groups may be present in the aldehydes and ketones used and these groups may contain any desired substituents such as halogen atoms, other alkyl or aryl groups, and diverse functional groups. Preferably, the selected aldehyde or ketone contains only carbon, hydrogen and oxygen atoms (from hydroxyl, acid, ester and ether linkages as well as the carbonyl group) and is limited to not more than about 20 carbon atoms for practical purposes. Representative examples of this broad area available for selection will appear hereinafter in the specific examples that have been prepared and studied.

The beta dione component may also be selected from a large number of possibilities so long as the requisite beta dione structure is present in the molecule. By beta dione structure is meant a structure in which two keto groups are separated by one carbon atom, as for example in the following structure:

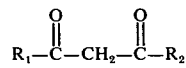

in which the carbonyl carbon atoms are bonded to other than hydrogen. The beta dione selected contains not more than about 20 carbon atoms for practical purposes. Preferably, $R_1$ and $R_2$ of the beta dione are the same or different alkyl, cycloalkyl, or aryl groups which may contain non-interfering substituents such as the halogens. The rings may contain substituents such as alkyl groups if desired. Typical examples of beta diones are: 2,4-pentanedione, 2,4-hexanedione, 3,5-heptanedione, 7,9-octadecanedione, 5,7-decanedione-2,4-dimethyl, and the like. Typical beta diones containing cyclic groups are 1,3-butanedione-1-phenyl and 1-cyclohexanone-2-acetyl.

In general, the end product is prepared by reacting the selected aldehyde or ketone such as methyl ethyl ketone and the beta dione such as 2,4-pentanedione with aqueous hydrogen peroxide in a hydrophilic fluid media. Conveniently, the reaction is executed in a mutual solvent or dispersant and the hydrogen peroxide is added as an aqueous solution. The conversion of the ketones to the organic peroxides is conventional with sufficient aqueous hydrogen peroxide being added to form at least appreciable organic peroxides therewith. A stoichiometric excess of hydrogen peroxide is generally used to insure completeness of the reaction. In general, the desired reaction is accelerated by heating the mixture to about 25°–45° C., preferably about 30°–35° C. Depending upon the quantities, the preparative equipment and other factors, the reaction will be completed within a number of hours.

The reaction is suitably catalyzed by the addition of an acid catalyst such as sulfuric acid but the catalyst preferably takes the form of an acidic ion exchange resin. The catalyst is suitably removed at the completion of the reaction. The reaction acidic conditions but this factor may be adequately met by the aqueous hydrogen peroxide which is acidic. The addition of acid or acidic ion exchange resin further promotes the reaction in most cases. An optimum product with respect to stability is obtained where the pH of the end reaction product is adjusted to about 4.0–5.5, preferably 4.5. Organic amines such as the heterocyclic amineslike pyridine have been found to be advantageous for adjusting the pH.

The amounts of the various components of the final composition are subject to some variation. The water content should usually be at least about 18% in the final composition where fire resistance is sought but may be lower in some cases and may be as high as desired, consistent with practicality which demands a composition of sufficiently high peroxide content to render rapid catalysis of resin systems.

The proportion of the selected aldehyde or different ketone to beta dione is relatively critical. Best results are achieved where the selected aldehyde or different ketone is used in a ratio of 1 mole of beta dione to about 3–20 equivalent weights of the selected aldehyde or different ketone based upon the number of co-reactive carbonyl sites therein. About 3–5 equivalent weights of the selected aldehyde or different ketone has given optimum results with the materials used to date.

"Equivalent weight" is used in the usual sense. For example, methyl ethyl ketone contains one coreactive carbonyl group and 3–5 moles should be used for each mole of a beta dione. In the case of a polyfunctional non-beta ketone such as 2,5-hexanedione having two coreactive carbonyl groups, only about 1.5–2.5 moles are needed for each mole of beta dione.

In general, only aldehyde and ketone carbonyl groups are coreactive with the beta dione and hydrogen peroxide in the present invention. One exception to this rule has been found in the carbonyl group of a beta keto ester. In this special case the carbonyl group from the carboxyl group has been found to function as an aldehyde or ketone carbonyl group in addition to its ketone carbonyl group for coreaction with a beta dione and hydrogen peroxide. Accordingly, acetoacetate esters are considered as having two coreactive carbonyl groups when determining the amount to be used in the present process. It should be understood that both carbonyl groups need not be reacted unless desired. If reaction of the keto carbonyl groups only is desired, the full molar quantity of about 3–5 moles of the acetoacetate ester is employed for each mole of 2,4-pentanedione and the ester is considered as having only one coreactive carbonyl group. Similarly, all carbonyl groups of other non-beta aldehydes and ketones need not be reacted by appropriately limiting the proportions of reactants.

In the preferred fire resistant compositions, sufficient mutual solvent or dispersant is added to the composition to achieve a homogeneous or non-separating composition. This will depend upon the proportion of the other ingredients and the type of materials used. In most cases the solvent or dispersant will constitute the balance of the composition in addition to the water and organic peroxides. Preferred proportions for the composition are about 18–20% water, about 30% solvent or dispersant and about 50–52% peroxides. In these ranges a composition having an active oxygen content of about 10–11% can be obtained.

The mutual solvents or dispersants include those described in said U.S. Pat. No. 3,507,800. In general, a preferred group of materials can be classified as water soluble aliphatic, preferably hydrocarbon, polyoxy alkanes and ester, although any mutual solvent or dispersant capable of forming a homogeneous composition with the water and the organic peroxide and which does not react therewith to destroy the peroxide-water nature of the composition may be used. It appears that the crucial aspect of the useable materials for purposes of homogenation is the presence of a plurality of oxygen atoms. Thus, polyalkylene glycols, such as polyethylene glycol, polypropylene glycol and other aliphatic polyhydroxy compounds which are liquid or soluble in water and which will dissolve or disperse both the peroxide and water or render them mutually miscible, are contemplated within the scope of the present invention. Other suitable polyoxy solvents and dispersants include water soluble polyethers, polyepoxies, polyaldehydes and polyketones since they all contain the requisite oxygen and are aliphatic in nature, provided of course that they are a mutual solvent or dispersant for the peroxide in water and are inert thereto.

As noted, the mutual solvent or dispersant may be a polyoxy alkane or a polyoxy ester. The ester group provides the requisite plural oxygen atoms and may be present alone or in addition to the other types of polyoxy linkages noted above. Thus, suitable solvents or dispersants include esters such as ethylene glycol monoethyl ether acetate, diethylene glycol monoethyl ether acetate, methoxy triglycol acetate, polypropylene carbonate, trimethyl phosphate, silicate esters and the like.

The following example will illustrate the general method of preparation of the new compositions:

EXAMPLE I

In a suitable glass round bottom flask, fitted with agitator, reflux condenser and thermometer were charged:
30 g. Polypropylene Glycol 425
24 g. Methyl Ethyl Ketone
6 g. 2,4-Pentanedione
9 g. Dowex 50 WX-8

The mixture was cooled to 12.0°C. and 40 g. of 50% w $H_2O_2$ was added over a period of 45–50 minutes. The temperature was maintained at 30°–35° C. and the reaction continued for 16 hours. Upon completion of the reaction, the catalyst was removed by filtration and the pH of the resultant liquid peroxide formulation adjusted to 4.0 to 5.5, preferably 4.5 using pyridine and measuring apparent pH on a Leeds & Northrup pH meter. The resultant peroxide was then treated to remove excess water and concentrate the peroxide to an active oxygen content of 10.50 to 10.55%. The composition was about
18% $H_2O$
30% Polypropylene Glycol 425
52% Aliphatic hydrocarbon ketone peroxides A large scale pilot plant run was conducted in the following manner:

EXAMPLE II

Into a 30 gallon glass lined pfaudler reactor, equipped with agitator, temperature probe and fume exhaust were charged:
40 lbs. 5 oz. Polypropylene Glycol 425
8 lbs. 1 oz. 2,4-Pentanedione
32 lbs. 4 oz. Methyl Ethyl Ketone
12 lbs. Dowex 50WX-8

The materials were mixed and, by use of a brine bath circulated through the jacket of the reactor, cooled to 15° C. Then 58 lbs. 8 oz. of 50%w $H_2O_2$ were charged over a period of 1.25 hours, maintaining the temperature at 33°–35° C. by jacket cooling. The reaction was continued for 21 hours, maintaining the temperature. Upon completion of the reaction, the reactants were filtered to remove catalyst. The peroxide solution of about 18 gallons in volume was adjusted to pH 4.5 with 105 ml. of reagent grade pyridine. The partially dried finished product had the following composition:

| | |
|---|---|
| Active Oxygen: | 10.50% |
| Polypropylene Glycol 425: | 30.00% |
| Aliphatic Hydrocarbon Ketone Peroxides: | 52.00% |
| Water: | 18.00% |

A sample of the material of Example II was forwarded to the Bureau of Explosives for testing. The Bureau of Explosives determined the flash point of the material to be above 100° F. and to not detonate under blasting cap initiation. The Bureau also determined that the sample did not become ignited readily by external flame. When a porous wick was placed in a portion of the sample and ignited, the sample (which is a clear transparent water-white liquid) burned fairly steadily without noticeable acceleration until nearly exhausted when some flaming occurs. The Bureau of Explosives held the sample to not be subject to classification as an oxidizing material under Interstate Commerce Commission regulations.

To demonstrate the advantageous performance of the new compositions in catalyzing polyester resin systems, a series of experiments were performed. For comparison, a standard commercial grade of methyl ethyl ketone peroxide (MEKP) was employed together with a fire resistant methyl ethyl ketone peroxide (FR-MEKP) prepared in accordance with the teachings of the previously referenced U.S. Pat. No. 3,507,800. The material prepared in Example II was used as representative of the present invention.

The following Table lists catalyst performance with a series of commercially available polyester resins together with the promoters used where applicable and the amount of catalyst employed. The bath temperature is the temperature of the medium surrounding the vessel in which the polymerization reaction was executed. The Table shows the resin temperature at the commencement of the reaction, the peak temperature of the reaction, and the time to reach the peak temperature. As is well understood, a high peak temperature, especially where the reaction is run in a low temperature environment, and a short time to reach the peak temperature are the desired attributes of a good catalyst.

TABLE I

Resin: Hetron 92
Promoter = 0.5%w Cobalt Naphthenate 6%
Catalyst = 1.0%w

A. Bath Temperature = 9.0° C.

| Catalyst | MEKP | FR-MEKP | EXAMPLE II |
|---|---|---|---|
| Resin Temperature | 10.0°C. | 10.0°C. | 10.0°C. |
| Peak Temperature | 132.3°C. | 130.0°C. | 136.8°C. |
| Peak Time | 40'00" | 43'00" | 26'00" |

TABLE I-continued

Resin: Hetron 92
B. Bath Temperature = 25.0°C.

| Catalyst | MEKP | FR-MEKP | EXAMPLE II |
|---|---|---|---|
| Resin Temperature | 25.0°C. | 25.0°C. | 25.0°C. |
| Peak Temperature | 157.0°C. | 154.0°C. | 157.8°C. |
| Peak Time | 15'00" | 15'00" | 11'00" |

Resin: Plaskon PE 258
Catalyst = 1.0%

A. Bath Temperature = 7.0°C.

| Catalyst | MEKP | FR-MEKP | EXAMPLE II |
|---|---|---|---|
| Resin Temp., °C. | 10.0 | 10.0 | 10.0 |
| Peak Temp., °C. | 138.0 | 124.8 | 138.0 |
| Peak Time | 124'00" | 100'00" | 81'00" |

B. Bath Temperature = 9.0°C.

| Catalyst | MEKP | FR-MEKP | EXAMPLE II |
|---|---|---|---|
| Resin Temp., °C. | 10.0 | 10.0 | 10.0 |
| Peak Temp., °C. | 143.0 | 140.0 | 142.0 |
| Peak Time | 105'00" | 79'00" | 68'00" |

C. Bath Temperature = 13.0°C.

| Catalyst | MEKP | FR-MEKP | EXAMPLE II |
|---|---|---|---|
| Resin Temp., °C. | 14.5 | 14.5 | 14.5 |
| Peak Temp., °C. | 147.4 | 133.8 | 147.0 |
| Peak Time | 77'00" | 61'00" | 52'00" |

D. Bath Temperature = 23.0°C.

| Catalyst | MEKP | FR-MEKP | EXAMPLE II |
|---|---|---|---|
| Resin Temp., °C. | 23.0 | 23.0 | 23.0 |
| Peak Temp., °C. | 166.2 | 163.3 | 163.0 |
| Peak Time | 34'00" | 32'00" | 24'00" |

Resin: Sherwin-Williams US9UA61
Catalyst = 1.0%w

A. Bath Temperature = 5.0°C.

| Catalyst | MEKP | FR-MEKP | EXAMPLE II |
|---|---|---|---|
| Resin Temp., °C. | 8.2 | 8.3 | 8.7 |
| Peak Temp., °C. | 10.3 | 12.5 | 46.2 |
| Peak Time | Over 5 hours | Over 5 hours | 2 hrs. 45 mins. |

B. Bath Temperature = 11.0°C.

| Catalyst | MEKP | FR-MEKP | EXAMPLE II |
|---|---|---|---|
| Resin Temp., °C. | 14.8 | 14.8 | 14.8 |
| Peak Temp., °C. | 15.2 | 18.0 | 144.8 |
| Peak Time | Over 2 hours | Over 2 hours | 70'00" |

C. Bath Temperature = 13.0°C.

| Catalyst | MEKP | FR-MEKP | EXAMPLE II |
|---|---|---|---|
| Resin Temp., °C. | 19.0 | 19.0 | 19.0 |
| Peak Temp., °C. | 152.9 | 137.5 | 158.0 |
| Peak Time | 111'00" | 86'00" | 43'00" |

D. Bath Temperature = 23.0°C.

| Catalyst | MEKP | FR-MEKP | EXAMPLE II |
|---|---|---|---|
| Resin Temp., °C. | 24.0 | 24.0 | 24.0 |
| Peak Temp., °C. | 163.0 | 167.8 | 171.3 |
| Peak Time | 62'00" | 45'00" | 26'00" |

The following example illustrates the necessity for forming a co-reaction peroxide product of the selected aldehyde or different ketone such as methyl ethyl ketone and the beta dione such as 2,4-pentanedione. Thus, when 2,4-pentanedione is added to preformed methyl ethyl ketone peroxide, the catalyst performance is substantially inferior to a catalyst prepared in accordance with the present invention. In this experiment, four samples of ketone peroxides were prepared and are identified as follows:

EXAMPLE III

A. A portion of the material prepared in accordance with Example II (52% active peroxide).

B. A commercial methyl ethyl ketone peroxide (60% active peroxide).

C. A commercial methyl ethyl ketone peroxide to which has been added 1% by weight of 2,4-pentanedione (59% active peroxide).

D. A commercial methyl ethyl ketone peroxide to which has been added 5% by weight of 2,4-pentanedione (55% active peroxide).

The above four catalysts were then used for curing the referenced polyester resins. All materials were used on an equal weight basis. The figures given for gel time represent the time until a gel structure was formed from the starting polyester resin. The other notations are used as before.

TABLE II

1. Resin: Polylite 8224A
   Temperature = 25.0°C.      Catalyst = 0.5%w

| Catalyst | A | B | C | D |
|---|---|---|---|---|
| Gel Time | 7'30" | 33'30" | 39'45" | 45'20" |
| Peak Time | 16'00" | 47'00" | 53'00" | 58'00" |
| Peak Temp., °C. | 155.0 | 153.0 | 152.8 | 156.0 |

2. Resin: ADM 7531MT16
   Temperature = 25.0°C.      Catalyst = 0.5%w

| Catalyst | A | B | C | D |
|---|---|---|---|---|
| Gel Time | 18'00" | 27'00" | 26'00" | 21'00" |
| Peak Time | 38'30" | 57'00" | 52'00" | 38'00" |
| Peak Temp., °C. | 143.0 | 135.0 | 136.5 | 145.0 |

3. Resin: Co Rezyn 277W
   Temperature = 25.0°C.      Catalyst = 0.5%w

| Catalyst | A | B | C | D |
|---|---|---|---|---|
| Gel Time | 19'00" | 25'00" | 28'00" | 36'00" |
| Peak Time | 40'00" | 48'00" | 52'00" | 57'00" |
| Peak Temp., °C. | 112.0 | 132.0 | 133.5 | 137.0 |

4. Resin: Hetron 92
   Temperature = 25.0°C.      Catalyst = 0.5%w
   Promoter - 0.5%w Cobalt Naphthenate 6%

| Catalyst | A | B | C | D |
|---|---|---|---|---|
| Gel Time | 7'00" | 15'15" | 15'00" | 14'00" |
| Peak Time | 17'00" | 28'00" | 27'00" | 23'30" |
| Peak Temp., °C | 154.0 | 149.0 | 152.0 | 157.0 |

The following experiments illustrate the advantageous properties of the present compositions as influenced by a variation in the ratio of the selected aldehyde or different ketone such as methyl ethyl ketone to beta dione such as 2,4-pentanedione in the preparation of them. The work demonstrates the significant advantage of a composition in which the aldehyde or different ketone (methyl ethyl ketone) is used in a proportion relative to the beta dione (2,4-pentanedione) in the preparation of the organic peroxide composition or close to the preferred ratio of about 3–5:1.

EXAMPLE IV

Three fire resistant compositions were prepared in accordance with the method and techniques of Example II but utilizing the proportion of materials listed below. Composition A contains a 4:1 weight ratio (5.5:1 molar ratio) of methyl ethyl ketone to 2,4-pentanedione with compositions B and B being variations thereof.

A.  30.0 g. Polypropylene Glycol 425 (5.5:1 molar ratio)
     6.0 g. 2,4-Pentanedione
    24.0 g. Methyl Ethyl Ketone
     9.0 g. Dowex 50WX8
    43.5 g. H₂O₂ 50%w
B. 10% Increase of Difunctional Ketone (5.05:1 molar ratio)
    30.0 g. Polypropylene Glycol 425
     6.6 g. 2,4-Pentanedione
    24.0 g. Methyl Ethyl Ketone
     9.0 g. Dowex 50WX8
    44.82 g. H₂O₂ 50%w
C. 10% increase of Monofunctional Ketone (6.1:1 molar ratio)
    30.0 g. Polypropylene Glycol 425
     6.0 g. 2,4-Pentanedione
    26.4 g. Methyl Ethyl Ketone
     9.0 g. Dowex 50WX8
    46.86 g. H₂O₂ 50%w The above three materials were treated as in Example I. The finished products were then compared in a polyester resin system with the following results. A conventional methyl ethyl ketone peroxide was employed for comparative purposes. All materials are used on an equal weight basis.

Resin: Plaskon PE 258
Temperature = 21.0°C.

| Catalyst | A | B | C | MEKP |
|---|---|---|---|---|
| Gel Time | 13'15" | 13'45" | 14'00" | 15'45" |
| Peak Time | 27'00" | 27'14" | 27'45" | 32'00" |
| Peak Temp., °C. | 166.8 | 175.8 | 162.8 | 167.5 |

The following Example again shows the criticality of the ratio of the selected aldehyde or different ketone to beta dione together with the unexpected advantages obtained by using the 3–5:1 ratio of the preferred embodiment. In addition, the Example illustrates the criticality of executing the co-reaction with hydrogen peroxide as distinguished from organic peroxides such as t-butyl hydroperoxide.

EXAMPLE V

A series of peroxide co-reaction products were made from the materials shown in Table III below. The process used is essentially that of Example I except that the quantities of the materials used here are half that of Example I. Also, in this Example, the mixture was stirred in a flask in a water bath set at 44° C. for a period of 3 hours. The end product was adjusted to a pH of 5 with pyridine.

TABLE III

| | Molar Ratio of Methyl Ethyl Ketone to 2,4-Pentanedione |
|---|---|
| A.  15 gms Polypropylene Glycol<br>15 gms Methyl Ethyl Ketone<br>20 gms HOOH 50%<br>4.5 gms Ion Exchange Resin<br>   (Dowex 50WX-8) | — |
| B.  15 gms Polypropylene Glycol | |

TABLE III-continued

| | | Molar Ratio of Methyl Ethyl Ketone to 2,4-Pentanedione |
|---|---|---|
| | 1 gm 2,4-Pentanedione<br>14 gms Methyl Ethyl Ketone<br>20 gms HOOH 50%<br>4.5 gms Dowex 50WX-8 | 20:1 |
| C. | 15 gms Polypropylene Glycol<br>1.8 gms 2,4-pentanedione<br>13.2 gms Methyl Ethyl Ketone<br>20 gms HOOH 50%<br>4.5 gms Dowex 50WX-8 | 10:1 |
| D. | 15 gms Polypropylene Glycol<br>3.2 gms 2,4-pentanedione<br>11.8 gms Methyl Ethyl Ketone<br>20 gms HOOH 50%<br>4.5 gms Dowex 50WX-8<br>4.5 gms Dowex 50WX-8 | 5:1 |
| E. | 15 gms Polypropylene Glycol<br>4.7 gms 2,4-pentanedione<br>10.3 gms Methyl Ethyl Ketone<br>20 gms HOOH 50%<br>4.5 gms Dowex 50WX-8 | 3:1 |
| F. | 15 gms Polypropylene Glycol<br>6.1 gms 2,4-pentanedione<br>8.9 gms Methyl Ethyl Ketone<br>20 gms HOOH 50%<br>4.5 gms Dowex 50WX-8 | 2:1 |
| G. | 15 gms Polypropylene Glycol<br>3.2 gms 2,4-pentanedione<br>11.8 gms Methyl Ethyl Ketone<br>20 gms Tert Butyl Hydroperoxide<br>4.5 gms Dowex 50WX-8 | 5:1 |

The above compositions were then checked for gel time and time-temperature performance with the polyester resin known as Hetron 92. 35 grams of Hetron resin was combined with 0.5%wt. of each of the peroxide compositions of Table III together with 0.5%wt. of cobalt octanoate (6%). The initiated resin in a 1 oz. container was maintained in a water bath at a temperature of 24° C. Temperatures of the resin were taken every few minutes and the results plotted on a curve. The results are shown in FIG. 1 of the accompanying drawings. The curve labeled A utilized composition A of Table III. The letters on the other curves correspond to formulations having the same letter in Table III.

As will be seen from FIG. 1, curve A with its relatively low peak temperature resulted from the use of MEK peroxide that does not have the benefit of the co-reaction process of this invention. Curves B through E represent performance curves of compositions prepared in accordance with this invention. The proportions of co-reactants of D and E, i.e. 3–5:1 represent the preferred embodiment. Curve F contains too little methyl ethyl ketone co-reactant and is outside the scope of this invention. While such a composition offers a high peak temperature, the shifting of the curve to the right, which indicates an increase in reaction time, is unacceptable because of the increased time. Curve G results from the use of an organic peroxide (t-butyl hydroperoxide) instead of hydrogen peroxide as required by the present invention. Such a composition is not suitable for the room temperature curing of polyesters and essentially fails to effect any cure at all. Hydrogen peroxide must be used in the present invention and organic peroxides cannot be substituted for it.

The following Examples illustrate the broad applicability of the invention to aldehydes and ketones in addition to the methyl ethyl ketone used in the preceding experimental work. Also illustrated is the use of other types of solvents and diluents in which to execute the preparative reaction and for storing and using the reaction product in combination therewith. By way of summary, the following types of aldehydes and ketones were prepared:

TABLE IV

Categories of Starting Materials For Co-reaction With Hydrogen Peroxide

1. Aliphatic Aldehyde and 2,4-Pentanedione
2. Aromatic Aldehyde and 2,4-Pentanedione
3. Methyl Ethyl Ketone and 2,4-Pentanedione prepared in an ester-type diluent
4. Keto-ester (other than beta keto ester) and 2,4-Pentanedione
5. Difunctional Ketone and 2,4-Pentanedione
6. Alkyl-aryl Ketone and 2,4-Pentanedione in an ester-type diluent
7. Beta keto ester and 2,4-Pentanedione
8. Alkyl - Branched chained alkyl ketone and 2,4-Pentanedione
9. Hydroxy substituted alkyl ketone and 2,4-Pentanedione
10. Methyl ethyl ketone in methyl carbitol solvent and 2,4-Pentanedione
11. Additional aliphatic ketone and 2,4-Pentanedione
12. Additional aliphatic ketone and 2,4-Pentanedione
13. Cyclic aliphatic ketone and 2,4-Pentanedione Specific compositions illustrating each of the Table III categories were prepared in accordance with the procedure described in Example I using the materials listed in the following Example. The approximate composition of the end reaction product is also indicated.

EXAMPLE VI

| Reactants | Weight Grams | Mole Ratio |
|---|---|---|
| 1. Methyl Carbitol | 20 | |
| 2-Ethyl Hexanal | 21.3 | 5.54 |
| 2,4-Pentanedione | 3 | 1.0 |
| Dowex 50WX-12 | 4.5 | |
| HooH-50% | 15 | excess |
| Approximate Composition | | |
| Ketone Peroxides | 54% | |

| Reactants | Weight Grams | Mole Ratio |
|---|---|---|
| Methyl Carbitol | 34% | |
| H₂O | 12% | |
| 2. Methyl Carbitol | 12.3 | |
| Benzaldehyde | 17.7 | 5.57 |
| 2,4-Pentanedione | 3 | 1.0 |
| Dowex 50WX-12 | 4.5 | |
| HooH-50% | 15 | excess |
| Approximate Composition | | |
| Ketone Peroxides | 60% | |
| Methyl Carbitol | 25% | |
| H₂O | 5% | |
| 3. Dimethyl Phthalate | 15 | |
| Methyl Ethyl Ketone | 12 | 5.55 |
| 2,4-Pentanedione | 3 | 1.0 |
| H₂SO₄ | 2 | |
| HooH-50% | 15 | excess |
| Approximate Composition | | |
| Ketone Peroxides | 60% | |
| Dimethyl Phthalate | 38% | |
| H₂O | 2% | |
| 4. Methyl Carbitol | 6 | |
| Ethyl Levulinate | 24 | 5.56 |
| 2,4-Pentanedione | 3 | 1.0 |
| Dowex 50WX8 | 4.5 | |
| HooH-50% | 15 | excess |
| Approximate Composition | | |
| Ketone Peroxides | 72% | |
| Methyl Carbitol | 13% | |
| H₂O | 15% | |
| 5. Methyl Carbitol | 17.5 | |
| 2,5-Hexanedione | 9.5 | 5.56 |
| 2,4-Pentanedione | 3 | 1.0 |
| Dowex 50WX-12 | 4.5 | |
| HooH-50% | 15 | |
| Approximate Composition | | |
| Ketone Peroxides | 44% | |
| Methyl Carbitol | 39% | |
| H₂O | 17% | |
| 6. Dimethyl Phthalate | 7 | |
| Acetophenone | 20 | 5.56 |
| 2,4-Pentanedione | 3 | 1.0 |
| H₂SO₄ | 2 | |
| HooH-50% | 15 | excess |
| Appproximate Composition | | |
| Ketone Peroxides | 65% | |
| Dimethyl Phthalate | 30% | |
| H₂O | | |

Benzophenone can be substituted for the acetophenone in this example with equivalent results.

| | | | |
|---|---|---|---|
| 7. Methyl Carbitol | 17 | | |
| Methyl Acetoacetate | 10 | 5.75 | |
| 2,4-Pentanedione | 3 | 1.0 | |
| Dowex 50WX-12 | 4.5 | | |
| HooH-50% | 15 | excess | |
| Approximate Composition | | | |
| Ketone Peroxides | 46% | | |
| Methyl Carbitol | 37% | | |
| H₂O | 17% | | |
| 8. Methyl Carbitol | 12 | | |
| Methyl Isobutyl Ketone | 16 | 5.33 | |
| 2,4-Pentanedione | 3 | 1.0 | |
| Dowex 50WX-12 | 4.5 | | |
| HOOH-50% | 15.0 | excess | |

| Reactants | Weight Grams | Mole Ratio |
|---|---|---|
| Approximate Composition | | |
| Ketone Peroxides | 58% | |
| Methyl Carbitol | 26% | |
| H₂O | 16% | |
| 9. Methyl Carbitol | 10.5 | |
| Diacetone Alcohol | 17.5 | 5.03 |
| 2,4-Pentanedione | 3 | 1.0 |
| Dowex 50WX-12 | 4.5 | |
| HOOH-50% | 15.0 | excess |
| Approximate Composition | | |
| Ketone Peroxide | 60% | |
| Methyl Carbitol | 23% | |
| H₂O | 17% | |
| 10. Methyl Carbitol | 15 | |
| Methyl Ethyl Ketone | 12 | 5.55 |
| 2,4-Pentanedione | 3 | 1.0 |
| Dowex 50WX-12 | 4.5 | |
| HOOH-50% | 15 | excess |
| Approximate Composition | | |
| Ketone Peroxides | 50% | |
| Methyl Carbitol | 34% | |
| H₂O | 16% | |
| 11. Methyl Carbitol | 17 | |
| Methyl Propyl Ketone | 14 | 5.42 |
| 2,4-Pentanedione | 3 | 1.0 |
| Dowex 50WX-12 | 4.5 | |
| HOOH-50% | 15 | excess |
| Approximate Composition | | |
| Ketone Peroxides | 50% | |
| Methyl Carbitol | 35% | |
| H₂O | 15% | |
| 12. Methyl Carbitol | 17.3 | |
| Acetone | 9.7 | 5.57 |
| 2,4-Pentanedione | 3.0 | 1.0 |
| Dowex 50WX-12 | 4.5 | |
| HOOH-50% | 15.0 | excess |
| Approximate Composition | | |
| Ketone Peroxides | 45% | |
| Methyl Carbitol | 38% | |
| H₂O | 17% | |
| 13. Methyl Carbitol | 11 | |
| Cyclohexanone | 16 | 5.44 |
| 2,4-Pentanedione | 3 | 1.0 |
| Dowex 50WX-12 | 4.5 | |
| HOOH-50% | 15.0 | excess |
| Approximate Composition | | |
| Ketone Peroxides | 59% | |
| Methyl Carbitol | 24% | |
| H₂O | 17% | |

All of the above catalysts exhibit the advantageous properties noted with respect to the methyl ethyl ketone 2,4-pentanedione peroxide discussed in the preceding examples. As typical of their performance, each of the catalysts of Example VI was used to initiate the polymerization of Plaskon PE 258 and was added thereto in a 1% by weight concentration. Bath temperatures are indicated.

The following Table shows the observed results. For comparison a standard methyl ethyl ketone peroxide (MEKP) was used to polymerize the same resin system and its performances is also shown. Catalyst numbers refer to the same number sequence used in Example VI.

TABLE V

| Bath Temperature = 21° C. | | | | | | | |
|---|---|---|---|---|---|---|---|
| Catalyst number | MEKP | 1. | 2. | 3. | 4. | 5. | 6. |
| Resin temperature, °C. | 21 | 21 | 21 | 21 | 21 | 21 | 21 |
| Peak temperature, °C. | 169 | 164.3 | 160.1 | 173 | 156 | 173.1 | 169.7 |
| Peak time | 35'30" | 24'30" | 30'00" | 30'30" | 29'30" | 30'30" | 33'00" |

| Bath Temperature = 5° C. | | | |
|---|---|---|---|
| Catalyst number | MEKP | 7. | 8. |
| Resin temperature, °C. | 21.5 | 21.5 | 21.5 |
| Peak temperature, °C. | 166 | 172 | 166 |
| Peak time | 31'00" | 18'30" | 29'00" |

| Bath Temperature = 23° C. | | | | |
|---|---|---|---|---|
| Catalyst number | MEKP | 9. | 10. | 11. |
| Resin temperature, °C. | 23.0 | 23.0 | 23.0 | 23.0 |
| Peak temperature, °C. | 166 | 169 | 165 | 164 |
| Peak time | 37'30" | 35'00" | 33'00" | 33'30" |

TABLE V-continued

| Bath Temperature = 21° C. | | | |
|---|---|---|---|
| Bath Temperature = 21° C. | | | |
| Catalyst number | MEKP | 12. | 13. |
| Resin temperature, °C. | 21.0 | 21.0 | 21.0 |
| Peak temperature, °C. | 168 | 164 | 174 |
| Peak time | 31'30" | 29'30" | 20'30" |

The following example illustrates the applicability of the invention to beta diones in addition to the 2,4-pentanedione used in the preceding experimental work. The additional beta diones used are typical of the results obtainable with all of the others within the generic scope previously defined.

EXAMPLE VII

Two compositions were prepared in accordance with the procedure described in Example I using the materials tabulated below. The approximate composition of the end reaction product is also indicated.

| Reactants | Weight Grams | Mole Ratio |
|---|---|---|
| 14. Methyl Carbitol | 14.6 | |
| Methyl Ethyl Ketone | 12 | 5.58 |
| 2,4-Hexanedione | 3.4 | 1.0 |
| Dowex 50WX-12 | 4.5 | |
| HOOH-50% | 15 | |
| Approximate Composition | | |
| Ketone Peroxides | 51% | |
| Methyl Carbitol | 32% | |
| H$_2$O | 17% | |
| 15. Methyl Carbitol | 14.2 | |
| Methyl Ethyl Ketone | 12 | 5.61 |
| 3,5-Heptanedione | 3.8 | 1.0 |
| Dowex 50WX-12 | 4.5 | |
| HOOH-50% | 15 | |
| Approximate Composition | | |
| Ketone Peroxide | 58% | |
| Methyl Carbitol | 40% | |
| H$_2$O | 2% | |

These catalysts exhibit the same advantageous properties noted with respect to the compositions containing 2,4-pentanedione in the preceding Examples. As typical of their performance, catalyst compositions 14 and 15 were used to initiate the polymerization of Plaskon PE 258 in a 1% by weight concentration at a bath temperature of 20° C. The following results were observed. For comparison a standard methyl ethyl ketone peroxide (MEKP) and catalyst composition number 10 of Example VI were used under the same conditions with the same resin.

| Catalyst | MEKP | 10 | 14 | 15 |
|---|---|---|---|---|
| Resin Temp., °C. | 20 | 20 | 20 | 20 |
| Peak Temp., °C. | 169 | 172 | 167 | 167 |
| Peak Time | 38'00" | 31'00" | 32'00" | 33'30" |

The following Example illustrates the criticality of co-reacting a beta dione with the selected other carbonyl compound in order to achieve the desired results.

EXAMPLE VIII

A series of co-reaction products were made in accordance with the procedure of Example I except that one-half the quantities of materials were used. The co-reaction was conducted in a 125 ml. flask in a constant temperature bath at 42° C. for 2 hours. The final reaction product pH adjusted was then used to cure Hetron polyester resin. In all cases 35 grams of resin was catalyzed with 0.5% wt. peroxide composition to which 0.5% wt. of cobalt octanoate (6%) was added. Polymerization conditions were maintained at 22°–23° C. The reactions were monitored and the results plotted as may be seen in FIGS. 2, 3 and 4 of the drawings. The materials used in making the peroxide compositions are shown in Table VI.

TABLE VI

| | Mole Ratio |
|---|---|
| A. 15 gms Polypropylene Glycol 425<br>2.5 gms 2,5-Hexanedione<br>12.5 gms Methyl Ethyl Ketone<br>20 gms HOOH 50%<br>4.5 gms Dowex 50WX-8 | 10:1 |
| B. 15 gms Polypropylene Glycol 425<br>1.8 gms 2,4-Pentanedione<br>13.2 gms Methyl Ethyl Ketone<br>20 gms HOOH 50%<br>4.5 gms Dowex 50WX-8 | 10:1 |
| A. 15 gms Polypropylene Glycol 425<br>3.6 gms 2,5-Hexanedione<br>11.4 gms Methyl Ethyl Ketone<br>20 gms HOOH 50%<br>4.5 gms Dowex 50WX-8 | 5:1 |
| B. 15 gms Polypropylene Glycol 425<br>3.2 gms 2,4-Pentanedione<br>11.8 gms Methyl Ethyl Ketone<br>20 gms HOOH 50%<br>4.5 gms Dowex 50WX-8 | 5:1 |
| A. 15 gms Polypropylene Glycol 425<br>5.2 gms 2,5-Hexanedione<br>9.8 gms Methyl Ethyl Ketone<br>20 gms HOOH 50%<br>4.5 gms Dowex 50WX-8 | 3:1 |
| B. 15 gms Polypropylene Glycol 425<br>4.7 gms 2,4-Pentanedione<br>10.3 gms Methyl Ethyl Ketone<br>20 gms HOOH 50%<br>4.5 gms Dowex 50WX-8 | 3:1 |

All of the compositions of Table VI designated as A contain a dione that is not a beta dione. All samples marked B contain the beta dione required by the present invention. Comparisons have been made at various ratios of the selected carbonyl compound (methyl ethyl ketone) relative to the dione. As may be seen from FIGS. 2–4, in all cases the compositions made with the requisite beta dione are vastly superior in performance as compared with the compositions which do not contain the beta dione.

Although the foregoing invention has been described in some detail by way of illustration and example for purposes of clarity of understanding, it is understood that certain changes and modifications may be practiced within the spirit of the invention as limited only by the scope of the appended claims.

What is claimed is:

1. An organic peroxide especially suitable for the room temperature curing of polyester resins made by the process comprising: concurrently reacting a beta dione of up to about 20 carbon atoms of the structure:

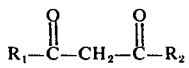

in which $R_1$ and $R_2$ are individually selected from the group consisting of alkyl, cycloalkyl, and aryl with a different carbonyl compound selected from the group consisting of ketones and aldehydes of up to about 20 carbon atoms free from aliphatic unsaturation and containing only carbon, hydrogen, and oxygen in a ratio of 1 mole of beta dione to about 3–20 equivalent weights of said different carbonyl compound based upon the number of co-reactive carbonyl groups therein in an acidic hydrophilic fluid media containing sufficient aqueous hydrogen peroxide to form appreciable amounts of organic peroxides therewith.

2. A product made in accordance with claim 1 wherein the ratio of beta dione to said different carbonyl compound is 1 mole of beta dione to about 3–5 equivalent weights of said different carbonyl compound.

3. A product made in accordance with claim 1 wherein an acidic ion exchange resin is added to said fluid media and is separated therefrom at the conclusion of the reaction.

4. A product made in accordance with claim 1 and including the step of adjusting the pH of the reaction product to about 4.0–5.5.

5. A product made in accordance with claim 1 and including the step of heating the reaction mixture to about 25°–45° C. to promote said concurrent reaction.

6. A product made in accordance with claim 1 wherein the reaction mixture contains sufficient water to impart fire resistance to the fluid media containing the reaction product.

7. A product made in accordance with claim 2 wherein said different carbonyl compound contains an aromatic group.

8. A product made in accordance with claim 2 wherein said different carbonyl compound is aliphatic.

9. A product made in accordance with claim 2 wherein said different carbonyl compound contains more than one carbonyl group for co-reaction so that its equivalent weight in said process is less than its molecular weight.

10. A product made in accordance with claim 2 wherein said different carbonyl compound is a ketone.

11. A product made in accordance with claim 2 wherein said different carbonyl compound is an aldehyde.

12. A product made in accordance with claim 2 wherein said different carbonyl compound is methyl ethyl ketone.

13. A product made in accordance with claim 2 wherein said different carbonyl compound is methyl acetoacetate.

14. A product made in accordance with claim 2 wherein said different carbonyl compound is methyl isobutyl ketone.

15. A product made in accordance with claim 2 wherein said different carbonyl compound is diacetone alcohol.

16. A product made in accordance with claim 2 wherein said different carbonyl compound is methyl propyl ketone.

17. A product made in accordance with claim 2 wherein said different carbonyl compound is acetone.

18. A product made in accordance with claim 2 wherein said different carbonyl compound is cyclohexanone.

19. A product made in accordance with claim 2 wherein said different carbonyl compound is 2-ethyl hexanal.

20. A product made in accordance with claim 2 wherein said different carbonyl compound is benzaldehyde.

21. A product made in accordance with claim 2 wherein said different carbonyl compound is ethyl levulinate.

22. A product made in accordance with claim 2 wherein said different carbonyl compound is 2,5-hexanedione.

23. A product made in accordance with claim 2 wherein said different carbonyl compound is acetophenone.

24. A product made in accordance with claim 2 wherein $R_1$ and $R_2$ are alkyl groups.

25. A product made in accordance with claim 2 wherein said beta dione is selected from the group consisting of 2,4-pentanedione, 2,4-hexanedione, and 3,5-heptanedione.

26. A product made in accordance with claim 2 wherein said beta dione is 2,4-pentanedione and said different carbonyl compound is methyl ethyl ketone.

* * * * *